United States Patent [19]

Gisby et al.

[11] Patent Number: 4,810,641

[45] Date of Patent: Mar. 7, 1989

[54] BIOCHEMICAL ASSAYS

[75] Inventors: Paul E. Gisby, Surbiton; Roger D. Newell, London; Peter B. Park, Walton on Thames, all of England

[73] Assignee: British Gas Corporation, London, England

[21] Appl. No.: 840,763

[22] Filed: Mar. 18, 1986

[30] Foreign Application Priority Data

Mar. 19, 1986 [GB] United Kingdom ............... 8507118

[51] Int. Cl.$^4$ .................... C12Q 1/32; C12Q 1/26
[52] U.S. Cl. ........................................ 435/26; 435/25; 435/29; 435/863
[58] Field of Search .................... 435/25, 29, 26

[56] References Cited

U.S. PATENT DOCUMENTS 4,162,942 7/1979 Gunther .......................... 435/17

OTHER PUBLICATIONS

Hovorka–Chem. Abst., vol. 78 (1973), p. 75525U.
Bergmeyer et al–Methods of Enzymatic Analysis–3rd edit. (1983), pp. 618–623.

Primary Examiner—Sam Rosen
Attorney, Agent, or Firm—Larson and Taylor

[57] ABSTRACT

Components of gaseous mixtures, which are present in the gas as a fluid, e.g. a gas, vapor or mist are assayed biochemically by conducting an enzymatic reaction wherein the fluid substrate is added to a liquid medium containing the enzyme. Particular reactions include the measurement of monoethylene glycol in natural gas employing a glycol dehydrogenase/NAD+ system and determing the amount of NAD+ reduced.

1 Claim, 1 Drawing Sheet

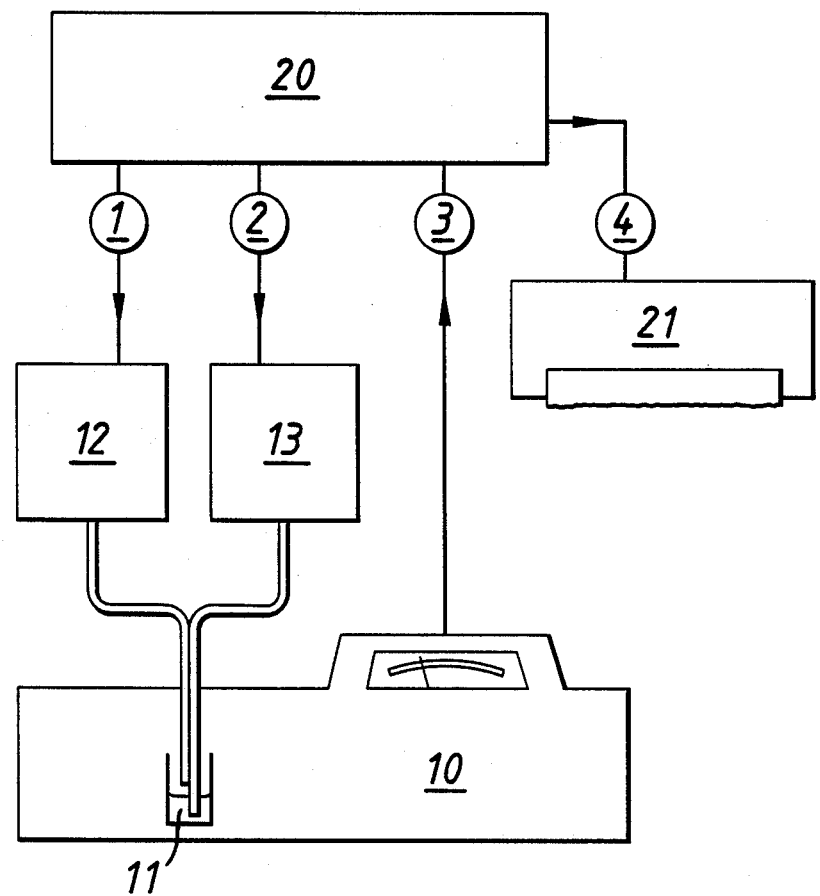

BIOCHEMICAL ASSAYS

This invention relates to methods for biochemical assays. More particularly the invention relates to the assay of fluid substrates especially those in which the fluid is in the form of a gas, vapour or aerosol.

The use of enzyme systems for biochemical assays is well known and many specific methods are known whereby a substrate is subjected to an enzymatic reaction in the presence of a substrate-specific enzyme and, sometimes, a co-enzyme and either the reaction product of the substrate or the changed co-enzyme are assayed.

In such assays it is common practice to add a suitably buffered solution or mixture containing the enzyme to a mixture or solution which contains both the substrate and the co-enzyme. This medium containing the substrate may also be suitably buffered.

We have now found that in those cases where the substrate itself is a fluid present as one phase in a multi-phase system, this substrate can be directly added to a mixture or solution which contains both the enzyme and any necessary co-enzyme for the reaction to be assayed.

Thus, the present invention provides a process for assaying an enzymatic reaction which includes the steps of adding a gaseous mixture which contains a fluid reaction substrate as the disperse or dilute phase in said mixture, to a liquid medium containing the enzyme for the reaction.

The process of the present invention may be used for biochemical assays wherein the substrate is a gas or liquid. For example the substrate may be a gas which is present as the dilute phase of a gas-gas system. Alternatively, the substrate may be a liquid present as the disperse phase in a liquid-gas system such as a vapour, a mist (or fog) or an aerosol.

The support materials for the particular enzymatic reaction, such as buffering agents, metal ions, co-enzymes are all contained in the medium containing the enzyme.

The process of the present invention may be used for the determination of alcohols such as glycols, e.g. 1,2-ethane diol or 1,2,3-propane triol (glycerol) and aldehydes e.g. formaldehyde or their oxidation products.

The process of the present invention is particularly suitable for oxidation of dehydrogenatable substrates such as glycols by oxidoreductase (otherwise known as dehydrogenase) enzymes wherein a co-enzyme such as nicotinamide adenine dinucleotide compound e.g. NAD itself is concomitantly reduced. In such a method the dehydrogenase may be present with $NAD^+$ in a suitably buffered liquid, e.g. aqueous medium, and the substrate is contacted with the medium, for example by shaking a known amount of medium in an atmosphere of defined volume, containing the substrate. Alternatively, the aqueous medium may contain only the coenzyme and buffer, the oxidoreductase only being added after mixing of the substrates with the medium.

The liquid medium (i.e. containing the reaction products) is recovered and assayed to determine the amount of NAD reduced to NADH. This may be effected by measurement of the absorbence of NADH between 325 and 355 nm, typically at 340 nm or by electrochemically oxidising the NADH back to NAD and measuring the current required, which is directly proportional to the concentration of NADH present.

In one application the process of the present invention may be employed to determine the concentration of 1,2-ethane diol, which is also known as mono-ethylene glycol (MEG), present in fuel gas such as natural gas or substitute natural gas.

MEG is employed as a conditioning agent for the packing materials employed in the joints of pipe sections. The MEG is normally added to the fuel gas being transported through the pipeline. Thus the MEG is carried in the gas and contacts the packing materials, where it is absorbed. In order to determine the effectiveness of the conditioning there is a need to monitor MEG in the gas at locations remote from the point of injection.

Certain mono ethylene glycol oxidoreductases or dehydrogenases (MEGDH) have been isolated which will oxidise MEG to glycol aldehyde, the proton generation being driven by the concomitant reduction of NAD according to the reaction.

$HO.CH_2.CH_2OH + NAD^+$ 

 $HO.CH_2CHO + NADH + H^+$

MEGDH is specific for glycols since it will not oxidize methanol which is normally co-present with the MEG in natural gas. MEGDH is also not inhibited by the sulphur compounds which are normally employed to odorise the fuel gas.

The enzyme can be isolated from certain strains of soil bacteria including a coryneform identified as Microbacterium sp. which has been deposited with the National Collection of Industrial Bacteria, Aberdeen, Scotland under the accession number NCIB 12048.

The present invention thus provides a process for the assay of glycols which comprises oxidising a glycol in the presence of a glycol oxidoreductase isolated from Microbacterium sp., deposited as NCIB 12048.

1. The colonial appearances is as follows;
   (i) Monethylene glycol agar (7 days, incubation at 30° C.) off-white in colour, entire, raised colony of 2.0–2.5 mm diameter
   (ii) Nutrient agar (4 days, incubation at 25° C.) White, round, regular, entire, opaque, smooth, shiny, low convex 2 mm diameter after 4 days incubation on nutrient agar.
2. Microscopic characterising features include: gram positive, non-motile, single, V and Y forms 3.0–4.0 $\mu$m long $\times$ 1.5–2.0 $\mu$m wide.—single cells The enzyme may be isolated by disruption of the bacterium cells and extraction. The isolated enzyme may be used in a liquid medium or may be immobilised on a membrane or solid support.

In the detection of MEG, predetermined volumes of fuel gas are taken. Such samples would be expected to contain up to 200 $mgm^{-3}$ MEG, typically, in excess of 10 $mgm^{-3}$ MEG. The gas would also contain up to 130 $mgm^{-3}$ of methanol and, for example 3:0.1 ppm (v/v) diethyl sulphide, 0.7 ppm ethyl mercaptan and 0.94 ppm t-butyl mercaptan, as odorants.

The enzyme medium is preferably an aqueous solution buffered to a pH between 7 to 10, more preferably about pH 9.0, and may contain $NAD^+$ at a concentration between up to 40 millimolar, typically between 10 to 20 millimolar. MEGDH may be present in amounts varying from 10 milliunits up to 1 unit, preferably more than 0.5 and more preferably up to 0.2 unit per ml of solution [one unit is amount of enzyme required to reduce 1 micromole of NAD+ per minute].

The present invention will be illustrated by reference to the accompanying drawing, which is a schematic representation of one form of the apparatus employed for the assay, and by the following Example.

EXAMPLE 1

MEG dehydrogenase was prepared from cells of Microbacterium sp. (NCIB 12048) as follows. A 30 hour old culture of cells was disrupted in a Stanstead Fluid Power cell disruptor. The cell debris was removed by passing the homogenate through a 0.1 micron Amicon hollow fibre filter. After concentration to a final volume of less than one liter, using a 30,000 dalton molecular weight cut-off hollow fibre filter, the homogenate was then taken to 80% ammonium sulphate saturation and left to stand overnight. The precipitate was then collected by centrifugation and redissolved in as small a volume as possible of Tris-HCl buffer (20 nM, pH 7.5). This mixture, which contained active exzyme, was diafiltered against more Tris-HCl, to remove the ammonium sulphate and then used as the enzyme solution in all assays.

A 100 ml sample of natural gas was taken up from the distribution network into a cell. The gas contained MEG of unknown concentration together with odorants comprising:

ethyl mercaptan: 0.9 ppm
Tert-butyl mercaptan: 0.6 ppm
Other mercaptans: 0.1 ppm
Diethyl sulphide: 7.6 ppm
Methyl ethyl sulphide: 1.0 ppm
Ethyl isopropyl sulphide: 1.6 ppm
Other sulphides: 0.6 ppm Into the cell was injected 2 ml of a 2 millimolar solution of NAD and the whole was shaken vigorously for thirty seconds.

Referring to the drawing, 0.9 ml of the shaken solution was transferred to a reaction cuvette 11 of a Pye-Unicam SP6 Spectrophotometer 10, linked to a microprocessor 20 via line 3. The microprocessor also controls a liquid dispenser 12 and an air pump 13 via links 1 and 2, respectively.

Within the liquid dispenser is contained a solution containing the glycol oxidoreductase in an initial concentration of 110 milliunits.ml$^{-1}$. Prior to the assay the activity of the enzyme is determined to calibrate the instrument. This is done by assaying standard MEG solutions and plotting the change in absorbance per unit time against MEG concentration. These weighting factors are held within the microprocessor.

In testing for MEG in the test sample, 100 microliters of the enzyme solution are added to the cuvette containing the shaken solution, after which air pumped in from pump 13 for three seconds to mix the reactants in the cuvette. The operation of the dispenser and pump are controlled by the microprocessor via links 2 and 3.

Once mixing has been completed a first absorbance reading is taken and recorded and, approximately six seconds later a second reading is made and recorded, the elapsed being accurately recorded by the microprocessor.

Using the data obtained from the calibrated test to weight previously inputted data on the rates of reaction, a calculation is performed on two measurements and the result, as a MEG concentration, of 5.40 mgm$^{-3}$ recorded with printer 21.

Another sample of the gas was taken and listed for MEG determination in a conventional manner.

A 100 ml gas sample was pulled through a stainless steel adsorption tube, using a syringe. The absorbent tube contained "Superpak 20M" which adsorbed any MEG in the gas. The tube was then put into a Perkin-Elmer automatic thermal desorber, where it was flushed with helium gas while being heated to 250° C. The helium passed from the adsorption tube to a 10° C. cold trap which contained "Tenax GC" to collect the MEG. After ten minutes, with helium still as the carrier, the MEG was flash desorbed from the "Tenax GC" by heating rapidly to 300° C. The MEG slug then passed to a Perkin-Elmer Sigma 115 gas chromatograph fitted with a 25 meter column of 0,2 mm i.d. The column packing was vitrous silica coated with carbowax 25M as the stationary phase. The amount of MEG was determined, by a flame ionisation detector fitted to the chromatograph, as being equivalent to a concentration in the original gas sample of 5 mg per cubic meter. The chromatograph had been previously calibrated using standard solutions of MEG in methanol.

We claim:

1. A process for determining the concentration of monoethylene glycol in natural gas, the process comprising contacting a predetermined volume of the gas with a reaction medium comprising a monoethylene glycol oxidoreductase and an NAD compound and determining the amount of NAD compound reduced concomitantly with the dehydrogenation of the glycol, said oxidoreductase comprising an enzyme isolated from Microbacterium sp deposited as NCIB 12048.

* * * * *